(12) United States Patent
Bajgrowicz et al.

(10) Patent No.: US 8,999,914 B2
(45) Date of Patent: Apr. 7, 2015

(54) CYCLOHEXENE- AND CYCLOPROPANATED CYCLOHEXENE- DERIVATIVES AS FRAGRANCES

(75) Inventors: Jerzy A. Bajgrowicz, Zürich (CH); Christopher Furniss, Bracknell (GB)

(73) Assignee: Givaudan S.A., Vernier (CH)

( * ) Notice: Subject to any disclaimer, the term of this patent is extended or adjusted under 35 U.S.C. 154(b) by 257 days.

(21) Appl. No.: 13/814,434

(22) PCT Filed: Aug. 11, 2011

(86) PCT No.: PCT/EP2011/063818
§ 371 (c)(1),
(2), (4) Date: May 20, 2013

(87) PCT Pub. No.: WO2012/020076
PCT Pub. Date: Feb. 16, 2012

(65) Prior Publication Data
US 2013/0303433 A1      Nov. 14, 2013

(30) Foreign Application Priority Data

Aug. 11, 2010   (GB) .................................. 1013474.0

(51) Int. Cl.
| | | |
|---|---|---|
| *C11B 9/00* | (2006.01) |
| *C07C 29/44* | (2006.01) |
| *C07C 31/137* | (2006.01) |
| *C07C 33/14* | (2006.01) |
| *C07C 45/69* | (2006.01) |
| *C07C 47/42* | (2006.01) |
| *C07C 49/543* | (2006.01) |

(52) U.S. Cl.
CPC .............. *C11B 9/0034* (2013.01); *C07C 29/44* (2013.01); *C07C 31/137* (2013.01); *C07C 33/14* (2013.01); *C07C 45/69* (2013.01); *C07C 47/42* (2013.01); *C07C 49/543* (2013.01); *C07C 2101/16* (2013.01); *C07C 2102/20* (2013.01); *C11B 9/0049* (2013.01); *C11B 9/0046* (2013.01)

(58) Field of Classification Search
USPC ............... 512/14, 22; 568/377, 446, 820, 826
See application file for complete search history.

(56) References Cited

U.S. PATENT DOCUMENTS

| | | |
|---|---|---|
| 3,514,489 A | 5/1970 | Lemberg |
| 7,642,385 B2 | 1/2010 | Kotachi et al. |
| 2010/0204084 A1 | 8/2010 | Goeke et al. |

FOREIGN PATENT DOCUMENTS

| | | | |
|---|---|---|---|
| JP | 61-015853 A | | 1/1986 |
| JP | 61015853 A | * | 1/1986 |
| WO | WO 2008/001668 A1 | | 1/2008 |
| WO | WO 2008001668 A1 | * | 1/2008 |
| WO | WO 2009/021342 A2 | | 2/2009 |

OTHER PUBLICATIONS

International Search Report mailed Jan. 31, 2012, for corresponding PCT International Patent Application No. PCT/EP2011/063818.
Written Opinion mailed Jan. 31, 2012, for corresponding PCT International Patent Application No. PCT/EP2011/063818.
International Preliminary Report on Patentability mailed Feb. 12, 2013, for corresponding PCT International Patent Application No. PCT/EP2011/063818.
Great Britain Search Report for Patent Application No. GB 1013474.0, mailed Nov. 26, 2010.

* cited by examiner

*Primary Examiner* — Ling Choi
*Assistant Examiner* — Lanee Reuther
(74) *Attorney, Agent, or Firm* — Curatolo Sidoti Co., LPA; Joseph G. Curatolo; Salvatore A. Sidoti

(57) ABSTRACT

1-(3/4-isobutyl-1/6-methylcyclohex-3-enyl)methanols and derivatives thereof having appreciable floral and hesperidic odor notes, their use as fragrance ingredient and perfumed products comprising them.

13 Claims, No Drawings

CYCLOHEXENE- AND CYCLOPROPANATED CYCLOHEXENE- DERIVATIVES AS FRAGRANCES

CROSS REFERENCE TO RELATED APPLICATIONS

This application is a national stage application of International Application No. PCT/EP2011/063818, filed 11 Aug. 2011, which claims priority from Great Britain Patent Application No. 1013474.0, filed 11 Aug. 2010, from which applications priority is claimed, and which are incorporated herein by reference.

The present invention relates to a novel class of compounds having appreciable floral and hesperidic odor notes and their use as fragrance ingredient. This invention relates furthermore to a method of their production and to fragrance compositions and perfumed products comprising them.

In the fragrance industry there is a constant demand for new compounds that enhance, modify or improve on odor notes. Floral bouquets have always been eagerly sought in the fragrance field, and many examples have been prepared and commercialised. Particularly desirable are floral rosy notes with hesperidic undertones.

It has now been found that 1-(3/4-isobutyl-1/6-methylcyclohex-3-enyl)methanols and derivatives thereof constitute a new, well-defined class of odorants exhibiting desirable floral and hesperidic odor characteristics making them particularly suitable for use as fragrance ingredients.

Accordingly, in a first aspect there is provided the use as fragrance of a compound of formula (I)

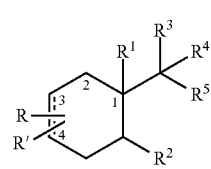

(I)

wherein
R is isobutyl at C-3 or C-4;
R' is hydrogen at C-3 or C-4 and the bond between C-3 and C-4 together with the dotted line represents a double bond; or
R' is —CH$_2$— and together with C-3 and C-4 represents a cyclopropane ring and the bond between C-3 and C-4 together with the dotted line represents a single bond;
R$^1$, and R$^2$ represent independently of each other a group selected from hydrogen, methyl and ethyl;
R$^3$ is selected from methyl and ethyl; and
R$^4$ is hydroxyl and R$^5$ is hydrogen; or
R$^1$, R$^2$ and R$^3$ represent independently of each other a group selected from hydrogen, methyl and ethyl, wherein at least one is not hydrogen, preferably two of which are not hydrogen; and
R$^4$ and R$^5$ together with the carbon atom to which they are attached represents a carbonyl.

Non-limiting examples are compounds of formula (I) wherein R$^4$ is hydroxyl and R$^5$ is hydrogen and R is bound to C-4.

Further non-limiting examples are compounds of formula (I) wherein R$^1$ and R$^3$ are methyl and R$^2$ is hydrogen or methyl.

Further non-limiting examples are compounds of formula (I) wherein R$^1$ and R$^2$ are methyl and R$^3$ is hydrogen or methyl.

Further non-limiting examples are compounds of formula (I) wherein R$^1$ is hydrogen, R$^2$ is methyl or ethyl, R$^4$ is hydroxyl and R$^5$ is hydrogen In particular embodiments compounds of formula (I) are selected from the group consisting of 4-isobutyl-1-methylcyclohex-3-enecarbaldehyde, 4-isobutyl-6-methylcyclohex-3-enecarbaldehyde, 4-isobutyl-1,6-dimethylcyclohex-3-enecarbaldehyde, 1-(4-isobutyl-1,6-dimethylcyclohex-3-enyl)ethanone, 1-(4-isobutyl-6-methylcyclohex-3-enyl)ethanol, 1-(4-isobutyl-1-methylcyclohex-3-enyl)ethanol, 1-(4-isobutyl-1,6-dimethylcyclohex-3-enyl)ethanol, 1-(4-isobutyl-6-methylcyclohex-3-enyl)propan-1-ol, 1-(6-isobutyl-3-methylbicyclo[4.1.0]heptan-3-yl)ethanol, and 1-(6-isobutyl-4-methylbicyclo[4.1.0]heptan-3-yl)ethanol.

The compounds of formula (I) may be used alone, as mixtures thereof, or in combination with a base material. As used herein, the "base material" includes all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

As used herein, "fragrance composition" means any composition comprising at least one compound of formula (I) and a base material, e.g. a diluent conventionally used in conjunction with odorants, such as dipropylene glycol (DPG), isopropyl myristate (IPM), triethyl citrate (TEC) and alcohol (e.g. ethanol), and known odorants.

The following list comprises examples of known odorant molecules, which may be combined with the compounds of the present invention:

essential oils and extracts, e.g. castoreum, costus root oil, oak moss absolute, geranium oil, tree moss absolute, basil oil, fruit oils such as bergamot oil and mandarine oil, myrtle oil, palmarose oil, patchouli oil, petitgrain oil, jasmine oil, rose oil, sandalwood oil, wormwood oil, lavender oil or ylang-ylang oil;

alcohols, e.g. cinnamic alcohol, cis-3-hexenol, citronellol, Ebanol™, eugenol, farnesol, geraniol, Javanol™, linalool, menthol, nerol, phenylethyl alcohol, rhodinol, Sandalore™, Super Muguet™, terpineol or Timberol™;

aldehydes and ketones, e.g. Azurone® (7-(3-methylbutyl)-1,5-benzodioxepin-3-one), anisaldehyde, α-amylcinnamaldehyde, Georgywood™, hydroxycitronellal, Iso E® Super, Isoraldeine®, Hedione®, Lilial®, maltol, methyl cedryl ketone, methylionone, verbenone or vanillin;

ethers and acetals, e.g. Ambrox™, geranyl methyl ether, rose oxide or Spirambrene™;

esters and lactones, e.g. benzyl acetate, Cedryl acetate, γ-decalactone, Helvetolide®, γ-undecalactone or Vetivenyl acetate;

macrocycles, e.g. Ambrettolide, ethylene brassylate or Exaltolide®;

heterocycles, e.g. isobutylquinoline.

The compounds according to formula (I) may be used in a broad range of perfumed products, e.g. in any field of fine and functional perfumery, such as perfumes, air care products, household products, laundry products, body care products and cosmetics. The compounds can be employed in widely varying amounts, depending upon the specific application and on the nature and quantity of other odorant ingredients. The proportion is typically from 0.0001 to 5 weight percent of the application. In one embodiment, compounds of the present invention may be employed in a fabric softener in an amount of from 0.0001 to 0.05 weight percent. In another embodiment, compounds of the present invention may be used in fine perfumery in amounts from 0.01 to 3 weight percent, more preferably between 0.5 and 2 weight percent. However, these values are given only by way of example, since the experienced perfumer may also achieve effects or may create novel accords with lower or higher concentrations, e.g. up to about 10 weight percent based on the perfumed product.

The compounds as described hereinabove may be employed in a consumer product base simply by directly mixing at least one compound of formula (I), or a fragrance composition with the consumer product base, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the consumer product base.

Thus, the invention additionally provides a method of manufacturing a perfumed product, comprising the incorporation of a compound of formula (I), as a fragrance ingredient, either by directly admixing the compound to the consumer product base or by admixing a fragrance composition comprising a compound of formula (I), which may then be mixed with a consumer product base, using conventional techniques and methods. Through the addition of an olfactorily acceptable amount of at least one compound of the present invention as hereinabove described the odor notes of a consumer product base will be improved, enhanced, or modified.

Thus, the invention furthermore provides a method for improving, enhancing or modifying a consumer product base by means of the addition thereto of an olfactorily acceptable amount of at least one compound of formula (I).

The invention also provides a perfumed product comprising:
a) as odorant at least one compound of formula (I); and
b) a consumer product base.

As used herein, "consumer product base" means a composition for use as a consumer product to fulfill specific actions, such as cleaning, softening, and caring or the like.

Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body-care products, e.g. shampoo, shower gel; air care products and cosmetics, e.g. deodorant, vanishing creme. This list of products is given by way of illustration and is not to be regarded as being in any way limiting.

To the best of our knowledge none of the compounds as defined by formula (I) herein above has been described in literature before. The closest analogues, from a structural point of view, are 5-(but-3-en-2-yl)-1-methylcyclohex-3-enecarbaldehyde which is described possessing a camphoraceous, herbaceaous pine odor (U.S. Pat. No. 3,514,489) and 4-isobutylcyclohex-3-enecarbaldehyde (JP 61-015853). However the later one is reported only as intermediate.

Thus, in a further aspect there is provided a compound of formula (I)

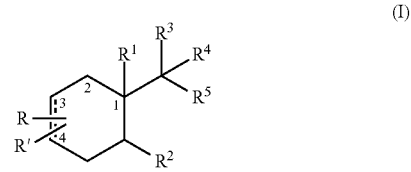

wherein
R is isobutyl at C-3 or C-4;
R' is hydrogen at C-3 or C-4 and the bond between C-3 and C-4 together with the dotted line represents a double bond; or
R' is —CH$_2$— and together with C-3 and C-4 represents a cyclopropane ring and the bond between C-3 and C-4 together with the dotted line represents a single bond;
R$^1$, and R$^2$ represent independently of each other a group selected from hydrogen, methyl and ethyl;
R$^3$ is selected from methyl and ethyl; and
R$^4$ is hydroxyl and R$^5$ is hydrogen; or
R$^1$, R$^2$ and R$^3$ represent independently of each other a group selected from hydrogen, methyl and ethyl, wherein at least one is not hydrogen, preferably two of which are not hydrogen; and
R$^4$ and R$^5$ together with the carbon atom to which they are attached represents a carbonyl.

The compounds of formula (I) may be prepared, as shown in scheme 1 below, starting from 5-methyl-3-methylenehex-1-ene 2 via Diels-Alder cycloaddition with an α,β-unsaturated aldehyde or ketone. This reaction may be carried out under thermal or catalytic conditions which influence the regio and stereoisomer ratio of the obtained cyclohexene derivatives 3 and 3'. The Diels-Alder reaction products are further transformed by α-alkylation (if R$^1$=H) and reduction or organometallic (e. g. Grignard or alkyllithium reagent) addition to give primary or secondary alcohols 4 and 4'. The alcohols may be cyclopropanated to result in further compounds of formula (I), according to the known Simmons-Smith or Yamamoto methodologies affording bicyclic alcohols 5 and 5'. Secondary alcohols 4+4' and 5+5' (R$^3$≠H) may be oxidised to ketones 3+3' and the corresponding bicyclic ketones respectively. The latter may be also obtained by direct cyclopropanation of 3+3'. Further particulars as to reaction conditions are provided in the examples.

Scheme 1:

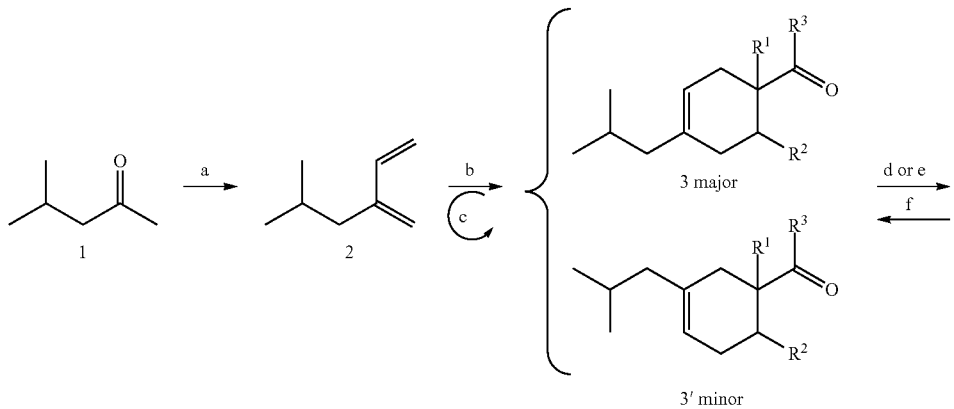

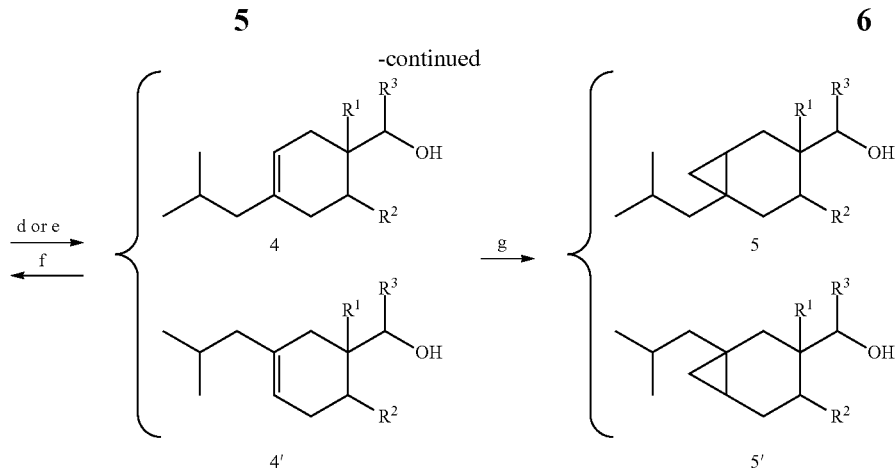

a) E.g. 1. vinylMgBr; 2. I$_2$ cat.; b)R$^2$CH═CR$^1$C(O)R$^3$, Δ or Lewis acid cat. (AlCl$_3$ or BF$_3$·Et$_2$O); c) KO$^t$Bu, R$^1$X; d) NaBH$_4$ or LiAlH$_4$;
e) R$^3$MgX; or R$^3$Li; f) Pyridinium dichromate; g) CH$_2$I$_2$, AlEt$_3$; or CH$_2$Br$_2$, Zn, CuBr, CH$_3$C(O)Br.

All products described in the examples are mixtures of regioisomers resulting from the "para" and "meta" orientation of the Diels-Alder cycloaddition (3-5 and 3'-5' respectively), the former being always major products. The ratio of regioisomers can be reduced or increased by changing the conditions of the Diels-Alder cycloaddition as known to one skilled in the art. All the products reported in the following examples are racemic mixtures. The enantiomer ratio of these mixtures can be easily changed by using chiral catalysts currently applied in asymmetric Diels-Alder reactions.

In a further aspect there is provided a process comprising the step of Diels-Alder cycloaddition of 5-methyl-3-methylenehex-1-ene to R$^2$CH═CR$^1$C(O)R$^3$ resulting in a composition comprising at least 60 weight % of a compound of formula (Ia)

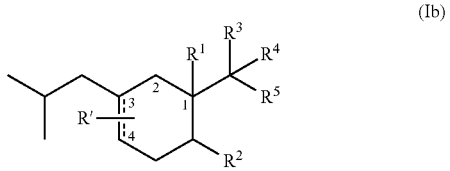
(Ia)

and up to 40 weight % of a compound of formula (Ib)

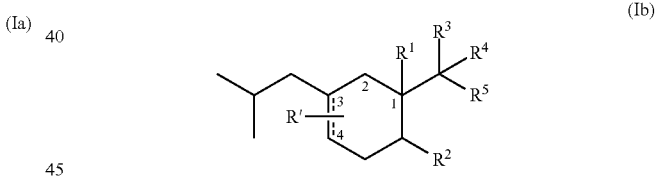
(Ib)

wherein
R' is hydrogen and the bond between C-3 and C-4 together with the dotted line represents a double bond;
R$^1$, R$^2$ and R$^3$ represent independently of each other a group selected from hydrogen, methyl and ethyl, wherein at least one is not hydrogen, preferably two of which are not hydrogen; and
R$^4$ and R$^5$ together with the carbon atom to which they are attached represents a carbonyl.

In a further embodiment there is provided a mixture containing at least 60 weight %, preferably at least 80 weight % (e.g. about 90-95 weight %), of a compound of formula (Ia)

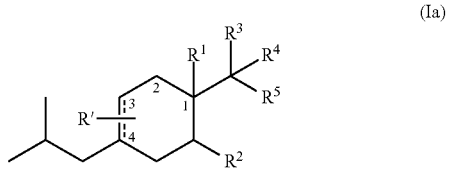
(Ia)

and up to 40 weight %, e.g. 10 to 30 weight %, of a compound of formula (Ib)

(Ib)

wherein
R' is hydrogen and the bond between C-3 and C-4 together with the dotted line represents a double bond; or
R' is —CH$_2$— and together with C-3 and C-4 represents a cyclopropane ring and the bond between C-3 and C-4 together with the dotted line represents a single bond;
R$^1$, and R$^2$ represent independently of each other a group selected from hydrogen, methyl and ethyl;
R$^3$ is selected from methyl and ethyl; and
R$^4$ is hydroxyl and R$^5$ is hydrogen; or
R$^1$, R$^2$ and R$^3$ represent independently of each other a group selected from hydrogen, methyl and ethyl, wherein at least one is not hydrogen, preferably two of which are not hydrogen; and
R$^4$ and R$^5$ together with the carbon atom to which they are attached represents a carbonyl.

The invention is now further described with reference to the following non-limiting examples. These examples are for the purpose of illustration only and it is understood that variations and modifications can be made by one skilled in the art.

The reported NMR spectra were measured in CDCl₃ at 400 MHz if not otherwise stated; chemical shifts (δ) are reported in ppm downfield from TMS; coupling constants J in Hz. The GC/MS analyses were run using a DB-5 column if not otherwise stated. Flash chromatography: *Brunschwig silica* gel 60 (32-63 mesh). Odor descriptions refer always to the mixture of isomers obtained by the last purification step reported in the examples.

EXAMPLE 1

4-Isobutyl-1-methylcyclohex-3-enecarbaldehyde
(3a)

Anhydrous AlCl₃ (0.6 g, 4.1 mmol) was suspended in toluene (250 ml) with vigorous stirring and a slow flow of nitrogen applied. Methacrolein (90% tech., 14 ml, 160 mmol) was added at room temperature over 10 min causing a slight increase in temperature. After stirring for 15 min, 5-methyl-3-methylenehex-1-ene 2 (25 g, 140 mmol) was added over 30 min causing the temperature to rise further to 31° C. The reaction mixture was stirred for 2 h and then quenched with sat. NaHCO₃ solution (200 ml). After brief agitation the phases were separated and the lower aqueous phase extracted with toluene (300 ml). The combined organic phases were washed with sat. sodium potassium tartrate solution (2×200 ml) and water (300 ml), dried (Na₂SO₄) and concentrated in vacuo. The oil was purified by short Vigreux distillation at reduced pressure to give 3a as a colorless oil (12 g, 48% yield) containing ca. 10% GC of an isomer 3'a.

3a: $^1$H NMR: δ 9.48 (s, 1H), 5.36 (sb, 1H), 2.35 (d, J=16.7, 1H), 1.99-1.91 (m, 2H), 1.89-1.78 (m, 4H), 1.70 (nonet, 1H), 1.50 (dt, J=12.9, 6.8, 1H), 1.04 (s, 3H), 0.83 (d, J=6.6, 3H), 0.81 (d, J=6.6, 3H). $^{13}$C NMR: δ 206.0 (d), 136.6 (s), 119.3 (d), 47.4 (t), 44.4 (s), 31.7 (t), 29.0 (t), 26.0 (d), 25.0 (t), 22.4 (q), 22.3 (q), 20.6 (q). MS: 180 (30, M⁺), 123 (56), 109 (33), 95 (100), 93 (41), 91 (31), 81 (64), 79 (32), 67 (40), 43 (67), 41 (44).

3'a: MS: 180 (4, M⁺), 151 (44), 109 (26), 95 (100), 93 (33), 91 (26), 81 (47), 67 (27), 57 (26), 43 (32), 41 (35).

Odor description: citrus, hesperidic, floral, marine with orange pith, watery, watermelon, anisic, woody dry and coconut shell aspects.

EXAMPLE 2

4-Isobutyl-6-methylcyclohex-3-enecarbaldehyde
(3b)

Crotonaldehyde cis/trans (16 g, 230 mmol) was dissolved in methylene chloride and cooled to −30° C. With stirring, and under nitrogen, BF₃.OEt₂ (3.6 ml, 29 mmol) was added gradually. A solution of 5-methyl-3-methylenehex-1-ene 2 (21 g, 191 mmol) in methylene chloride (50 ml) was then added at −30° C. over 1 h and the pot allowed to warm to −20° C. The solution was stirred at this temperature for a further 1.5 h before being poured onto 2M NaOH (100 ml). After brief agitation the phases were separated and the lower organic phase washed with water (100 ml) and brine (2×100 ml). The combined aqueous phases were extracted with MTBE (150 ml), phase separated and the upper organic part washed to neutral with brine. The organic phases were combined, dried (Na₂SO₄) and concentrated in vacuo to afford 3b as a pale yellow oil (33 g, 94% yield; 98% pure). The product was used in the next steps without further purification.

$^1$H NMR: δ 9.63 (d, J=3.0, 1 H), 5.36 (sb, 1H), 2.32-1.99 (m, 5H), 1.86-1.60 (m, 4H), 1.03 (d, J=6.3, 3H), 0.83 (2d, J=6.3, 6H). $^{13}$C NMR: δ 205.3 (s), 136.4 (s), 118.7 (d), 52.5 (d), 47.4 (t), 35.1 (t), 28.3 (d), 25.9 (d), 23.9 (t), 22.5 (q), 22.3 (q), 19.7 (q). MS: 180(36, M⁺), 123 (49), 95 (78), 93 (64), 91 (42), 67 (42), 57 (100), 55 (42), 43 (37), 41 (61).

Odor description: floral, aldehydic, citrus, hesperidic, fruity, marine with watery, melon, fatty, orange pith and juicy aspects.

EXAMPLE 3

4-Isobutyl-1,6-dimethylcyclohex-3-enecarbaldehyde
(3c)

4-Isobutyl-6-methylcyclohex-3-enecarbaldehyde 3b (8 g, 44 mmol) was dissolved in methylene chloride (400 ml) and cooled to −3° C. with stirring and under nitrogen. KO$^t$Bu (6.7 g, 58 mmol) and MeI (19 g, 130 mmol) were added sequentially and the suspension stirred for 30 min before being allowed to return to room temperature. After stirring for a further 3 h the reaction crude was poured onto brine (400 ml), stirred for 10 min and the phases allowed to separate. The upper aqueous phase was extracted with methylene chloride (150 ml) and the organic phases combined, dried (Na₂SO₄) and concentrated in vacuo to give 8.5 g of an orange oil (8.5 g). The oil was purified by flash chromatography (MTBE/hexane 1:9) and combination of pure fractions gave 3c as a 7:3 mixture of diastereomers (7 g, colorless oil, 80% yield). 1 g of the oil was distilled to give a sample for olfactory assessment. (0.52 g, colourless oil, >99% pure).

Major diastereoisomer: $^{13}$C NMR: δ 206.7 (d), 135.6 (s), 119.2 (d), 47.4 (t), 47.0 (s), 34.0 (d), 33.7 (t), 31.1 (t), 26.0 (d), 22.5 (q), 22.3 (q), 20.3 (q), 16.2 (q). MS: 194 (11, M⁺), 109 (100), 95 (39), 93 (20), 91 (22), 82 (43), 81 (29), 67 (23), 57 (21), 43 (34), 41 (37).

Minor diast.: $^{13}$C NMR: δ 206.7 (d), 135.9 (s), 118.3 (d), 48.0 (s), 47.3 (t), 33.4 (t), 31.7 (t), 31.1 (d), 26.0 (d), 22.6 (q), 22.2 (q), 16.0 (q), 13.7 (q). MS: 194 (12, M⁺), 109 (100), 107 (28), 95 (47), 91 (26), 82 (25), 81 (31), 67 (26), 57 (29), 43 (38), 41 (44).

Odor description: fruity, floral, green, lactonic, fatty.

EXAMPLE 4

1-(4-Isobutyl-6-methylcyclohex-3-enyl)ethanol (4b)

4-Isobutyl-6-methylcyclohex-3-enecarbaldehyde 3b (23 g, 130 mmol) was dissolved in diethyl ether (200 ml). The solution was cooled to −20° C. under nitrogen and MeLi (1.6M, 100 ml, 160 mmol) added over 30 min with stirring. The temperature was allowed to rise to −5° C. and the reaction stirred at this temperature for 1 h. The reaction mixture was poured slowly, and under nitrogen, onto a vigorously stirred mixture of sat. NH₄Cl (150 ml) and ice (100 g). After stirring for 15 min the phases were separated and the lower aqueous layer extracted with diethyl ether (100 ml). The organic phases were combined, washed with water (100 ml), dried (Na₂SO₄) and concentrated in vacuo to give 24 g of a light yellow oil. The crude oil was purified by flash chromatography (MTBE/hexane 1:3) to give 4b as a 3:2 mixture of diastereomers (18 g, 72% yield, colorless oil, >99% pure). Subsequent distillation provided 12.5 g of olfactory pure product.

Major diast.: $^1$H NMR (C₆D₆, 500 MHz): δ 5.41 (sb, 1H), 3.84 (m, 1H), 2.12 (m, 1H), 1.92 (m, 1H), 1.90-1.77 (m, 3H), 1.76-1.62 (m, 2H), 1.56 (m, 1H), 1.01 (m, 1H), 0.96 (d, J=6.5, 3H), 0.94 (d, J=6.7, 3H), 0.90 (d, J=6.5, 3H), 0.89 (d, J=6.6, 3H), 0.57 (db (OH), J=4.9, 1H). $^{13}$C NMR (C₆D₆, 500 MHz): δ 135.8 (s), 121.8 (d), 66.3 (d), 47.9 (t), 45.8 (d), 37.3 (t), 29.9

(d), 26.2 (d), 23.7 (t), 22.9 (q), 22.5 (q), 21.2 (q), 19.5 (q). MS: 196 (18, M+), 178 (41), 135 (77), 121 (38), 107 (40), 95 (47), 93 (100), 79 (38), 57 (73), 43 (30), 41 (29).

Minor diast.: $^1$H NMR (C$_6$D$_6$, 500 MHz): δ 5.37 (m, 1H), 3.77 (m, 1H), 2.14 (m, 1H), 1.92 (m, 1H), 1.90-1.67 (m, 5H), 1.56 (m, 1H), 1.31 (tt, J=8.2, 5.8, 1 H), 0.94 (d, J=6.6, 3H), 0.89 (2d, J=6.5, 6H), 0.86 (d, J=6.6, 3H), 0.63 (db (OH), J=4.9, 1H). $^{13}$C NMR (C$_6$D$_6$, 500 MHz): δ 135.8 (s), 121.3 (d), 67.8 (d), 47.9 (t), 45.9 (d), 36.5 (t), 29.8 (d), 26.2 (d), 24.2 (t), 22.8 (q), 22.5 (q), 19.5 (q), 18.7 (q). MS: 196 (30, M+), 178 (46), 135 (81), 121 (45), 107 (46), 95 (74), 93 (100), 79 (39), 57 (75), 43 (39), 41 (34).

Odor description: citrus, hesperidic, floral, green with rhubarb and grapefruit aspects.

EXAMPLE 5

1-(4-Isobutyl-1-methylcyclohex-3-enyl)ethanol (4c)

4-Isobutyl-1-methylcyclohex-3-enecarbaldehyde 3a (20 g, 111 mmol) was dissolved in diethyl ether (120 ml) and the solution stirred under nitrogen. An ice-bath was used to keep the temperature below 20° C. while MeMgBr (3M, 48 ml, 144 mmol) was added over 30 min. The ice-bath was removed and the reaction stirred for a further 30 min before being poured slowly, and under nitrogen, onto 2M HCl (50 ml). The phases were separated and the upper organic phase washed twice with brine (2×100 ml), dried (MgSO$_4$) and concentrated in vacuo to give 19.6 g of a colorless oil. The product was purified by distillation (0.1 mbar, 90° C.) to give 4c as a 4:5 mixture of diastereomers containing 6.5% of a third isomer (14 g, 52% yield, colourless oil, 95% pure).

2 main diast.: $^1$H NMR (C$_6$D$_6$, 500 MHz): δ 5.37 (m, 1H), 5.32 (m, 1H), 3.37-3.29 (m, 2H), 2.09 (db, J=17.1, 1H), 1.93-1.65 (m, 12H), 1.59-1.47 (m, 2H), 1.44-1.35 (m, 2H), 1.20 (dddd, J=12.8, 5.8, 4.0, 1.8, 1H), 0.99-0.92 (m, 2H (2OH)), 0.97 (d, J=6.4, 3H), 0.94 (d, J=6.4, 3H), 0.89 (d, J=6.6, 3H), 0.88 (d, J=6.6, 3H), 0.87 (2d, J=6.6, 6H), 0.83 (2s, 6H). $^{13}$C NMR (C$_6$D$_6$, 500 MHz): δ 135.9 (s), 135.4 (s), 121.4 (d), 121.0 (d), 74.2 (d), 74.1 (d), 47.9 (2t), 36.1 (s), 36.0 (s), 34.6 (t), 34.0 (t), 31.0 (t), 30.4 (t), 26.4 (d), 26.3 (d), 25.6 (2t), 22.9 (2q), 22.5 (2q), 18.3 (q), 18.1 (q), 17.7 (q), 17.5 (q).

Major diast. (52%): MS: 196 (7, M+), 178 (45), 135 (99), 107 (60), 95 (100), 93 (63), 91 (28), 81 (38), 79 (46), 57 (36), 43 (33).

Minor diast. (42%): MS: 196 (7, M+), 178 (46), 135 (100), 107 (66), 95 (97), 93 (69), 91 (31), 81 (37), 79 (48), 57 (43), 43 (34).

3$^{rd}$ isomer (6.5%): MS: 196 (5, M+), 136 (30), 135 (41), 107 (35), 95 (100), 93 (52), 91 (28), 79 (45), 57 (80), 43 (38), 41 (29).

Odor description: floral, fruity, green with freesia, osmanthus, peach skin, plum and rhubarb aspects.

EXAMPLE 6

1-(4-Isobutyl-1,6-dimethylcyclohex-3-enyl)ethanol (4d)

4-Isobutyl-1,6-dimethylcyclohex-3-enecarbaldehyde 3c (4.5 g, 23 mmol) was dissolved in diethyl ether (40 ml). The solution was cooled to 0-5° C. under nitrogen and MeMgBr (3M, 12 ml, 35 mmol) added over 40 min with stirring. The temperature was allowed to rise to room temperature and stirring continued for 30 min. The reaction mixture was poured slowly onto a vigorously stirred mixture of 2M HCl and ice. After stirring for 10 min the phases were separated and the lower aqueous layer extracted twice with MTBE. The organic phases were combined and washed with sat. NaHCO$_3$ solution and brine to pH 7. After drying (MgSO$_4$) the organic phase was concentrated in vacuo to give 4.6 g of a light yellow oil. The crude oil was purified by flash chromatography (MTBE/hexane 3:7) to give 4d as a 1:2:3:5 mixture of diastereomers (2.7 g, 55% yield, >98% pure). Distillation of a 0.7 g sample gave 0.6 g of 4d (colorless oil, >99% pure) for olfactory assessment.

Major diast.: $^{13}$C NMR: δ 133.9 (s), 119.1 (d), 71.3 (d), 47.7 (t), 37.9 (s), 33.8 (t), 31.9 (d), 31.7 (t), 26.0 (d), 22.6 (q), 22.4 (q), 17.6 (q), 16.5 (q), 15.4 (q).

1st eluted GC peak (45%) MS: 210 (3, M+), 109 (100), 107 (37), 95 (38), 93 (46), 82 (36), 67 (29), 57 (51), 45 (27), 43 (50), 41 (38).

2$^{nd}$ eluted GC peak (55%) MS: 210 (2, M+), 109 (100), 107 (59), 95 (40), 93 (74), 82 (34), 67 (34), 57 (90), 45, (34), 43 (61), 41 (51).

Odor description: floral, fatty, fruity, green with rhubarb and bitter grapefruit aspects.

EXAMPLE 7

1-(4-Isobutyl-6-methylcyclohex-3-enyl)propan-1-ol (4e)

4-isobutyl-6-methylcyclohex-3-enecarbaldehyde 3b (0.5 g, 2.8 mmol) was dissolved in diethyl ether (10 ml). The solution was cooled to 0-5° C. under nitrogen and EtMgBr (3M, 1.4 ml, 4.2 mmol) added over 10 min with stirring. The temperature was allowed to rise to room temperature and the reaction stirred for 10 min. The reaction mixture was poured slowly onto a vigorously stirred mixture of 2M HCl and ice. After stirring for 15 min the phases were separated and the lower aqueous layer extracted twice with MTBE. The organic phases were combined and washed with sat. NaHCO$_3$ solution and brine to give a neutral pH. After drying (MgSO$_4$) the organic phase was concentrated in vacuo to give 0.6 g of oil. The oil was purified by flash chromatography (MTBE/hex.1:4) to give 4e as a 2:85:8:4 mixture of diastereomers (0.54 g, 91% yield, colorless oil, >99% pure). Subsequent distillation provided an olfactory pure sample (0.4 g).

Major diast.: $^{13}$C NMR: δ 136.0 (s), 121.1 (d), 72.4 (d), 47.4 (t), 43.6 (d), 37.3 (t), 29.7 (d), 27.6 (t), 26.0 (d), 23.3 (t), 22.6 (q), 22.3 (q), 19.3 (q), 10.6 (q). MS: 210 (2, M+), 192 (40), 149 (70), 107 (71), 95 (53), 93 (96), 91 (27), 79 (39), 57 (100), 43 (37), 41 (42).

Odor description: green, fatty, floral, rosy with dried leaves and rhubarb aspects.

EXAMPLE 8

1-(6-Isobutyl-3-methylbicyclo[4.1.0]heptan-3-yl)ethanol (5a)

Diiodomethane (27 g, 102 mmol) was added to a solution of 1-(4-isobutyl-1-methylcyclohex-3-enyl)ethanol 4c (10 g, 51 mmol) in hexane (100 ml) at room temperature. The reaction mixture was cooled to 5° C. and triethylaluminium (1M, 102 ml, 102 mmol) added under nitrogen over 30 min whilst maintaining a temperature below 10° C. The reaction was allowed to return to room temperature and stirred overnight. Analysis by GC showed that ca. 25% of the alkene remained unreacted and so a further portion of diiodomethane (13.5 g, 50 mmol) and triethyl aluminium (1M, 51 ml, 51 mmol) were added sequentially at room temperature. The reaction was continued for a further 8 h after which time the reaction mixture was poured carefully onto ice-water (100 ml) under nitrogen. MTBE (200 ml) and 2M NaOH (100 ml) were added and the mixture stirred for 15 min. After phase separation the lower aqueous layer was extracted with MTBE (200 ml) and the organic layers combined, washed with water (200 ml), 2M HCl (100 ml) and twice with water (100 ml). The organic layer was dried ($Na_2SO_4$) and the solvent removed in vacuo to give 15 g of a yellow oil. The crude oil was purified by flash chromatography (silica gel, MTBE/hex. 3:7) and distillation to give 5a as a 1:2:4 mixture of diastereomers (9 g, 80% yield, colorless oil, >95% pure).

GC sniff allowed identification the main contributor to the odor as the minor isomer, 13% abundant. Subsequent GC trapping and HSQC NMR analysis allowed us to isolate and confirm its structure as one of the epimers of 1-((1RS,3SR,6SR)-6-isobutyl-3-methylbicyclo[4.1.0]heptan-3-yl)ethanol.

The two major isomers (25+45%) in the mixture were determined, in a similar way, to be epimeric of 1-((1RS,3RS,6SR)-6-isobutyl-3-methylbicyclo[4.1.0]heptan-3-yl)ethanol.

1-((1SR,3SR,6RS)-6-isobutyl-3-methylbicyclo[4.1.0]heptan-3-yl)ethanol

Major diast.: $^1$H NMR ($C_6D_6$, 500 MHz): δ 3.02 (m, 1H), 1.80 (m, 1H), 1.68 (m, 1H), 1.61-1.53 (m, 2H), 1.48 (ddd, J=13.6, 8.8, 2.3, 1H), 1.31 (ddt, J=13.3, 5.5, 2.4, 1H), 1.22 (d, J=13.6, 1H), 0.93 (d, J=6.6, 3H), 0.89 (d, J=6.6, 3H), 0.87 (d, J=6.4, 3H), 0.80 (td, J=13.3, 5.3, 1H), 0.79 (s, 3H), 0.63-0.58 (m (inc. OH), 2H), 0.54-0.42 (m, 2H), 0.08 (m, 1H). $^{13}$C NMR ($C_6D_6$, 500 MHz): δ 75.5 (d), 51.2 (t), 35.8 (s), 33.1 (t), 27.6 (t), 26.4 (d), 24.2 (q), 23.8 (t), 22.5 (q), 18.2 (q), 18.0 (t), 17.4 (s), 17.4 (q), 14.9 (d). MS (GC separation on a VF-Waxms column): 210 (1, M$^+$), 149 (46), 136 (40), 109 (100), 107 (43), 95 (58), 93 (97), 81 (46), 69 (35), 67 (62), 43 (45).

Minor diast.: $^1$H NMR ($C_6D_6$, 500 MHz): δ 3.05 (m, 1H), 1.80 (m, 1H), 1.75-1.65 (m, 2H), 1.61-1.53 (m, 2H), 1.25 (d, J=13.5, 1H), 1.00-0.86 (m, 2H), 0.93 (d, J=6.6, 3H), 0.89 (2d, J=6.6, 6H), 0.80 (s, 3H), 0.67 (db (OH), J=4.4, 1H), 0.59 (dd, J=13.5, 1.7, 1H), 0.54-0.42 (m, 2H), 0.08 (m, 1H). $^{13}$C NMR ($C_6D_6$, 500 MHz): δ 75.8 (d), 51.2 (t), 35.9 (s), 32.8 (t), 28.1 (t), 26.5 (d), 24.2 (q), 23.8 (t), 22.5 (q), 18.5 (q), 18.1 (t), 17.6 (q), 17.4 (s), 14.9 (d). MS (GC separation on a VF-Waxms column): 210 (1, M$^+$), 149 (44), 121 (38), 109 (100), 107 (50), 95 (61), 93 (91), 81 (48), 69 (35), 67 (62), 43 (43).

1-((1RS,3SR,6SR)-6-isobutyl-3-methylbicyclo[4.1.0]heptan-3-yl)ethanol $^1$H NMR ($C_6D_6$, 500 MHz): δ 3.75 (qd, J=6.4, 5.7, 1H), 2.46 (m, 1H), 1.76 (m, 1H), 1.61-1.54 (m, 2H), 1.39 (td, J=13.5, 5.5, 1H), 1.16 (ddt, J=14.1, 5.5, 2.7, 1H), 0.95 (dd, J=14.2, 2.5, 1H), 0.94 (d, J=6.4, 3H), 0.92 (d, J=6.6, 3H), 0.88 (d, J=6.6, 3H), 0.79 (td, J=13.8, 5.4, 1H), 0.68 (s, 3H), 0.59 (db (OH), J=5.7, 1H), 0.55-0.47 (m, 3H), 0.12 (m, 1H). $^{13}$C NMR ($C_6D_6$, 500 MHz): δ 68.4 (d), 51.2 (t), 35.3 (s), 34.6 (t), 31.3 (t), 26.5 (d), 24.3 (q), 24.2 (t), 22.4 (q), 21.5 (q), 20.0 (t), 17.6 (q), 17.3 (s), 15.3 (d). MS: 210 (27, M$^+$), 149 (56), 109 (97), 107 (61), 95 (73), 93 (100), 81 (60), 79 (48), 67 (70), 43 (59), 41 (47).

Odor description: floral, fruity, rosy with peach and lactonic dry aspects.

EXAMPLE 9

1-(6-Isobutyl-4-methylbicyclo[4.1.0]heptan-3-yl)ethanol (5b)

Diiodomethane (9.6 g, 36 mmol) was added at room temperature, with stirring and under nitrogen, to a solution of 1-(4-Isobutyl-6-methylcyclohex-3-enyl)ethanol 4b (3.5 g, 18 mmol) in hexane (50 ml). After cooling to 5° C. triethylaluminium (1M, 36 ml, 36 mmol) was added over 30 min while the temperature was kept below 5°. The reaction was allowed to return to room temperature and stirred for 16 h, then another portion of diiodomethane (9.6 g, 36 mmol) and triethylaluminium (1M, 36 ml, 36 mmol) were added. After a further 15 h yet more diiodomethane (4.8 g, 18 mmol) and triethylaluminium (1M, 18 ml, 18 mmol) were added. After 2 h stirring, the reaction being still incomplete, the reaction mixture was poured slowly, onto a stirred mixture of ice and water. The phases were separated and the aqueous one extracted twice with hexane. The combined organic layers were washed with water, twice with 2M HCl and again with water, dried ($Na_2SO_4$) and the solvent removed in vacuo. The crude oil (5.7 g) was dissolved in methylene chloride (50 ml) and solid 3-chloroperbenzoic acid (ca. 77%, 1.5 g, 6.7 mmol) was added in four portions under nitrogen. The mild exothermic effect was controlled with a cool water bath. The reaction was stirred till the unreacted 4b had been completely consumed (30 min). 2M NaOH was added and the mixture stirred until it became white. The phases were separated and the upper aqueous layer extracted twice with methylene chloride. The combined organic layers were washed twice with 2M NaOH and water, dried ($MgSO_4$) and evaporated in vacuo to give 4.6 g of oil. The crude oil was purified by flash chromatography (MTBE/hex. 3:2) and combination of pure fractions gave 5b as a 1:1.1:1.8 mixture of diastereomers (3.4 g, 86% yield, colourless oil, 95% pure). Subsequent distillation provided an olfactory pure sample.

Major diast. (45%): $^{13}$C NMR: δ 67.1 (d), 50.4 (t), 43.2 (d), 39.6 (t), 30.7 (d), 26.4 (d), 23.1 (q), 22.8 (q), 21.9 (t), 20.6 (q), 19.4 (q), 19.2 (d), 18.5 (t), 17.8 (s). MS: 210 (1, M$^+$), 149 (39), 135 (32), 107 (100), 93 (53), 79 (31), 67 (34), 55 (35), 45 (34), 43 (48), 41 (42).

Second major diast. (27%): MS: 210 (1, M$^+$), 109 (29), 107 (100), 93 (38), 81 (27), 79 (25), 67 (32), 55 (30), 45 (31), 43 (42), 41 (36).

Minor diast. (24%): MS: 210 (2, M$^+$), 109 (25), 107 (100), 93 (41), 79 (25), 69 (27), 67 (29), 55 (28), 45 (28), 43 (39), 41 (35).

Odor description: fatty, floral, green with rhubarb, woody, rooty and vetiver aspects.

EXAMPLE 10

1-(4-Isobutyl-1,6-dimethylcyclohex-3-enyl)ethanone (3d)

1-(4-Isobutyl-1,6-dimethylcyclohex-3-enyl)ethanol 4d (2 g, 9 mmol) was dissolved in dimethylformamide (50 ml) and cooled to below 5° C. under nitrogen. Pyridinium dichromate (4.5 g, 12 mmol) was added in two portions with stirring and the reaction allowed to return to room temperature. After stirring for 90 min another portion of PDC (1 g, 2.7 mmol) was added and after a further 90 min the reaction was complete. The reaction mixture was poured onto ice-water and 2M HCl added. After brief agitation the product was extracted from the aqeuous phase with MTBE. The organic phases were combined and washed with sat. NaHCO3 solution then to pH 7 with brine. After drying ($Na_2SO_4$) the solvent was removed in vacuo to give 1.8 g of a crude oil which was purified by flash chromatography (MTBE/hexane 2:8). Combination of pure fractions gave 3d as a 7:3 mixture of diastereomers (1.5 g, 77% yield, 99% pure). Subsequent distillation provided a sample for olfactory assessment.

Major diast.: $^{13}$C NMR: δ 213.7 (s), 133.4 (s), 119.3 (d), 49.0 (s), 47.4 (t), 33.4 (d), 32.7 (t), 29.0 (t), 26.0 (d), 24.7 (q), 22.7 (q), 22.5 (q), 22.4 (q), 16.7 (q). MS: 208 (14, M$^+$), 165 (39), 109 (100), 107 (20), 95 (36), 91 (20), 82 (57), 81 (25), 67 (21), 43 (77), 41 (30).

Minor diast.: $^{13}$C NMR: δ 214.3 (s), 135.6 (s), 119.2 (d), 50.2 (s), 47.3 (t), 34.6 (t), 34.0 (t), 32.8 (d), 26.0 (d), 25.2 (q), 22.6 (q), 22.2 (q), 16.3 (q), 15.7 (q). MS: 208 (3, M$^+$), 165 (48), 109 (100), 107 (20), 95 (42), 91 (18), 82 (20), 81 (25), 67 (20), 43 (69), 41 (29).

Odor description: citrus, hesperidic, floral with bergamot aspects.

EXAMPLE 11

Hesperidic Floral Woody Perfuming Composition (Unisex)

| | parts per weight |
|---|---|
| Alpha Damascone @ 10% in DPG | 25 |
| Ambrofix (CAS 6790-58-5) | 10 |
| Benzyl Salicylate | 100 |
| Calone 1951 (7-methyl-2H-benzo[b][1,4]dioxepin-3(4H)-one) | 1 |
| Citronellyl Acetate | 10 |
| Cyclal C (2,4-dimethylcyclohex-3-enecarbaldehyde) @ 10% in DPG | 14 |
| Cyclohexal (4-(4-hydroxy-4-methylpentyl)cyclohex-3-enecarbaldehyde) | 55 |
| Gardenol (1-phenylethyl acetate) | 5 |
| Georgywood (2-acetyl-1,2,3,4,5,6,7,8-octahydro-1,2,8,8-tetramethylnaphthalene) Grapefruit Oil | 200 85 |
| Hedione (methyl 2-(3-oxo-2-pentylcyclopentyl)acetate) | 150 |
| (Z)-Hex-3-en-1-ol | 3 |
| (Z)-Hex-3-enyl acetate | 1 |
| Lemon Oil | 45 |
| Linalool | 15 |
| Linalyl Acetate (3,7-dimethylocta-1,6-dien-3-yl acetate) | 45 |
| Nirvanolide ((Z)-13-methyloxacyclopentadec-10-en-2-one) | 100 |
| Orange Oil | 15 |
| Pharaone (2-cyclohexylhepta-1,6-dien-3-one) @ 1% in DPG | 8 |
| Compound 4b (Example 4) | 25 |
| Dipropylene Glycol (DPG) | 88 |
| | 1000 |

The addition of 25 parts per weight of 1-(4-Isobutyl-6-methylcyclohex-3-enyl)ethanol to the composition brings volume and diffusion. It increases the floralcy of this accord, while enhancing the hesperidic top note with a grapefruit facet. The woody musky dry-down is highlighted with an impression of vetiver.

EXAMPLE 12

Floral Rose Perfuming Composition for Women

| | parts per weight |
|---|---|
| Adoxal (2,6,10-trimethylundec-9-enal) | 2 |
| Beta Damascone @ 10% in DPG | 35 |
| Cyclomethylene Citronellol (3-(4-methylcyclohex-3-enyl)butan-1-ol) | 8 |
| Elintaal (3-(1-ethoxyethoxy)-3,7-dimethylocta-1,6-diene) | 3 |

-continued

| | parts per weight |
|---|---|
| Ethyl Decadienoate | 7 |
| Ethyl Vanillin @ 10% in DPG | 1 |
| Eugenol | 5 |
| Galaxolide S | 20 |
| ((4S)-4,6,6,7,8,8-hexamethyl-1,3,4,6,7,8-hexahydrocyclopenta[g]isochromene) | 10 |
| Geranium Oil | |
| Geranyl Phenylacetate | 10 |
| Hedione (methyl 2-(3-oxo-2-pentylcyclopentyl)acetate) | 300 |
| (Z)-Hex-3-enyl acetate | 7 |
| Hexyl Cinnamic Aldehyde | 25 |
| Indol @ 1% in DPG | 45 |
| Moxalone @ 50% in TEC | 20 |
| (6,7-Epoxy-1,2,3,4,5,6,7,8-octahydro-1,1,2,4,4,7-hexamethylnaphthalene) | 3 |
| Peach Pure (5-heptyldihydrofuran-2(3H)-one) | |
| Pepperwood (3,7-dimethylocta-1,6-dien-3-yl dimethylcarbamate) | 200 |
| Phenylethyl Alcohol | 100 |
| Phenylethyl Cinnamate | 25 |
| Phenylethyl Salicylate | 25 |
| Rose de Mai Absolute | 1 |
| Toscanol (1-cyclopropylmethyl-4-methoxybenznene) @ 10% in DPG | 4 |
| Compound 5a (Example 8) | 55 |
| Dipropylene Glycol | 89 |
| | 1000 |

The addition of 55 parts per weight of 1-(6-Isobutyl-3-methylbicyclo[4.1.0]heptan-3-yl)ethanol to the composition brings a delicate and subtle natural floralcy. It soothes the ardent green top note, blends and reinforces the floral rosy heart while giving long-lastingness to the floral notes together with the powdery musky dry-down.

The invention claimed is:

1. A compound of formula (I)

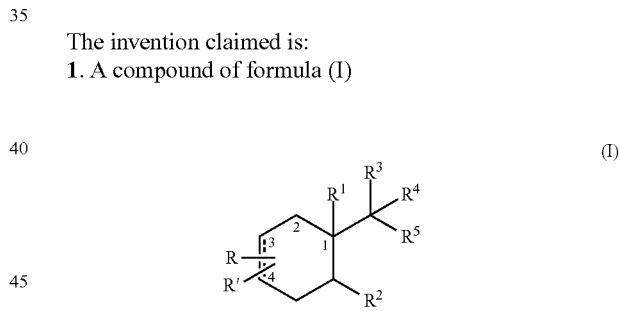

wherein
- R is isobutyl at C-3 or C-4;
- R' is hydrogen at C-3 or C-4 and the bond between C-3 and C-4 together with the dotted line represents a double bond; or
- R' is —CH$_2$— and together with C-3 and C-4 represents a cyclopropane ring and the bond between C-3 and C-4 together with the dotted line represents a single bond;
- R$^1$, and R$^2$ represent independently of each other a group selected from hydrogen, methyl and ethyl;
- R$^3$ is selected from methyl and ethyl; and
- R$^4$ is hydroxyl and R$^5$ is hydrogen; or
- R$^1$, R$^2$ and R$^3$ represent independently of each other a group selected from hydrogen, methyl and ethyl, wherein at least one is not hydrogen; and
- R$^4$ and R$^5$ together with the carbon atom to which they are attached represents a carbonyl.

2. A compound according to claim 1 wherein R is isobutyl at C-4.

3. A fragrance composition or a perfumed product comprising a compound of formula (I) as defined in claim 2, or a mixture thereof.

4. A perfumed product according to claim 3 wherein the perfumed product is selected from fine perfumery, fabric care, household products, personal care products, and air care products.

5. A compound according to claim 1 selected from the group consisting of 4-isobutyl-1-methylcyclohex-3-enecarbaldehyde, 4-isobutyl-6-methylcyclohex-3-ene carbaldehyde, 4-isobutyl-1,6-dimethylcyclohex-3-enecarbaldehyde, 1-(4-isobutyl-1,6-dimethylcyclohex-3-enyl)ethanone, 1-(4-isobutyl-6-methylcyclohex-3-enyl)ethanol, 1-(4-isobutyl-1-methylcyclohex-3-enyl)ethanol, 1-(4-isobutyl-1,6-dimethylcyclohex-3-enyl) ethanol, 1-(4-isobutyl-6-methylcyclohex-3-enyl)propan-1-ol, 1-(6-isobutyl-3-methyl bicyclo[4.1.0]heptan-3-yl)ethanol, and 1-(6-isobutyl-4-methylbicyclo[4.1.0]heptan-3-yl) ethanol.

6. A fragrance composition or a perfumed product comprising a compound of formula (I) as defined in claim 5, or a mixture thereof.

7. A perfumed product according to claim 6 wherein the perfumed product is selected from fine perfumery, fabric care, household products, personal care products, and air care products.

8. A fragrance composition or a perfumed product comprising a compound of formula (I) as defined in claim 1, or a mixture thereof.

9. A perfumed product according to claim 8 wherein the perfumed product is selected from fine perfumery, fabric care, household products, personal care products, and air care products.

10. A method for improving, enhancing or modifying a consumer product base comprising the step of adding thereto an olfactorily acceptable amount of at least one compound of formula (I) as defined in claim 1.

11. A method of using as fragrance, a compound of formula (I) as defined in claim 1, comprising incorporating the compound of formula (I) into a consumer product base as a fragrance ingredient, either by directly admixing the compound of formula (I) with the consumer product base or by admixing a fragrance composition comprising a compound of formula (I), which fragrance composition is then mixed with the consumer product base.

12. A mixture containing at least 60 weight % of a compound of formula (Ia)

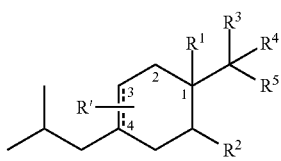

(Ia)

and up to 40 weight % of a compound of formula (Ib)

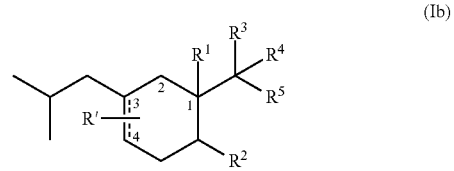

(Ib)

wherein
R' is hydrogen and the bond between C-3 and C-4 together with the dotted line represents a double bond; or
R' is —CH$_2$— and together with C-3 and C-4 represents a cyclopropane ring and the bond between C-3 and C-4 together with the dotted line represents a single bond;
R$^1$, and R$^2$ represent independently of each other a group selected from hydrogen, methyl and ethyl;
R$^3$ is selected from methyl and ethyl; and
R$^4$ is hydroxyl and R$^5$ is hydrogen; or
R$^1$, R$^2$ and R$^3$ represent independently of each other a group selected from hydrogen, methyl and ethyl, wherein at least one is not hydrogen; and
R$^4$ and R$^5$ together with the carbon atom to which they are attached represents a carbonyl.

13. A process comprising the step of Diels-Alder cycloaddition of 5-methyl-3-methylenehex-1-ene to R$^2$CH=CR$^1$C(O)R$^3$ resulting in a composition comprising at least 60 weight % of a compound of formula (Ia)

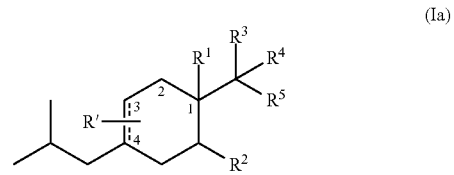

(Ia)

and up to 40 weight % of a compound of formula (Ib)

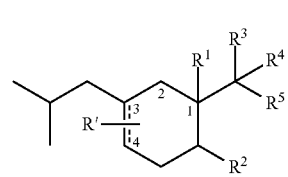

(Ib)

wherein
R' is hydrogen and the bond between C-3 and C-4 together with the dotted line represents a double bond;
R$^1$, R$^2$ and R$^3$ represent independently of each other a group selected from hydrogen, methyl and ethyl, wherein at least one is not hydrogen;
R$^4$ and R$^5$ together with the carbon atom to which they are attached represents a carbonyl.

* * * * *